United States Patent [19]
Roenigk

[11] Patent Number: 5,643,971
[45] Date of Patent: Jul. 1, 1997

[54] DURABLE ANTI-MICROBIAL AGENTS

[75] Inventor: Karl F. Roenigk, Hudson, Wis.

[73] Assignee: Minnesota Mining and Manufacturing Company, St. Paul, Minn.

[21] Appl. No.: 441,781

[22] Filed: May 16, 1995

Related U.S. Application Data

[62] Division of Ser. No. 301,043, Sep. 6, 1994, Pat. No. 5,541,233, which is a continuation of Ser. No. 983,685, Dec. 1, 1992, abandoned.

[51] Int. Cl.⁶ .................................................. C08L 1/00
[52] U.S. Cl. .................. 523/122; 106/18.36; 106/162.2
[58] Field of Search ............................... 106/18.36, 168; 523/122

[56] References Cited

U.S. PATENT DOCUMENTS

| | | | |
|---|---|---|---|
| 3,018,192 | 1/1962 | Hennemann | 117/98 |
| 3,586,520 | 6/1971 | Dillon | 106/15 |
| 3,594,221 | 7/1971 | Baldwin | 117/138.5 |
| 3,879,376 | 4/1975 | Vanierberghe et al. | 260/211 |
| 3,940,482 | 2/1976 | Grand | 424/245 |
| 3,953,608 | 4/1976 | Vanierberghe et al. | 424/361 |
| 4,048,181 | 9/1977 | Douglass | 260/294 |
| 4,122,084 | 10/1978 | Douglass | 260/294.8 |
| 4,122,085 | 10/1978 | Douglass | 260/294.8 |
| 4,307,089 | 12/1981 | Melloh et al. | 424/245 |
| 4,345,080 | 8/1982 | Bolich, Jr. | 546/6 |
| 4,396,766 | 8/1983 | Farmer, Jr. et al. | 546/6 |
| 4,443,222 | 4/1984 | Morris et al. | 8/189 |
| 4,528,283 | 7/1985 | Lang et al. | 514/55 |
| 4,533,736 | 8/1985 | Trotz et al. | 546/290 |
| 4,581,351 | 4/1986 | Berke et al. | 515/183 |
| 4,632,991 | 12/1986 | Maurer et al. | 546/6 |
| 4,659,700 | 4/1987 | Jackson | 514/55 |
| 4,659,830 | 4/1987 | Maurer et al. | 546/6 |
| 4,670,430 | 6/1987 | Imamura et al. | 514/188 |
| 4,845,204 | 7/1989 | Lang et al. | 536/20 |
| 4,957,908 | 9/1990 | Nelson | 514/55 |
| 5,015,632 | 5/1991 | Nelson | 514/55 |
| 5,114,984 | 5/1992 | Branch et al. | 521/121 |
| 5,173,535 | 12/1992 | Abrutyn | 525/54.3 |

FOREIGN PATENT DOCUMENTS

| | | |
|---|---|---|
| 0 149 175 | 7/1985 | European Pat. Off. . |
| 0 358 572 | 3/1990 | European Pat. Off. . |
| 1 576 698 | 7/1967 | France . |
| 2 259 111 | 6/1974 | Germany . |
| 72 050867 | 2/1964 | Japan . |
| 63-066243 | 3/1988 | Japan . |
| 2 145 630 | 6/1990 | Japan . |
| 2 153 723 | 6/1990 | Japan . |
| 1 202 716 | 8/1970 | United Kingdom . |
| 91/09163 | 6/1991 | WIPO . |
| 91 10435 | 7/1991 | WIPO . |
| 92 17285 | 10/1992 | WIPO . |

OTHER PUBLICATIONS

Chemical Patents Index, Basic Abstracts Journal, Section CH, Week 8734, Derwent Publications Ltd., London GB, Class C, AN 239024.
Chemical Abstracts, vol. 117, No. 8, 24 Aug. 1992, Columbus, OH abstract No. 71940b.
Rompp Chemie Lexikon, 1989, pp. 689–690.
Textile Research Institute Binding of Organic Antimicrobial Agents to Cotton Fabric as Zirconium Complexes, Morris et al., 1981, pp. 90–96.

*Primary Examiner*—Christopher Raimund
*Attorney, Agent, or Firm*—Gary L. Griswold; Walter N. Kirn; Daniel R. Pastirik

[57] ABSTRACT

The present invention comprises a metal complex capable of being dispersed in or alternatively, formed in a water-absorbing article. The metal complex consists of one or more metal ions, at least one chelating polymer chelated to the transition metal ion and at least one potentiator chelated to the transition metal ion. The chelating polymer may be a polyglucosamine, a polycarboxylic acid, a polyamine and methylene-acrylic acid polymer.

8 Claims, No Drawings

DURABLE ANTI-MICROBIAL AGENTS

This is a division of application No. 08/301,043 filed Sep. 6, 1994, now U.S. Pat. No. 5,541,233, which is a continuation of 07/983,685, filed Dec. 1, 1992, now abandoned.

FIELD OF INVENTION

The present invention relates to anti-microbial agents. In particular, the present invention relates to a sponge containing anti-microbial agents.

BACKGROUND OF THE INVENTION

Sponges are light, fibrous connective structures which have absorbent qualities. They can be made from a variety of different materials including polymers such as urethanes and cellulose in a number of different ways.

A preferred sponge is the cellulose sponge because of its excellent water sorption qualities. These sponges are made by dispersing sodium sulfate crystals in a viscose cellulose. Once mixed with the viscose cellulose, the sodium sulfate crystals are melted out of the sponge by heating the viscose cellulose while the viscose cellulose is regenerated or coagulated to an insoluble state. Once regenerated, the viscose cellulose sponge is rinsed.

Although exhibiting excellent water sorption qualities superior to other sponges, cellulose sponges have several drawbacks due to this characteristic. One drawback is that sponges can absorb moisture containing unwanted microorganisms such as bacteria and fungi. These microorganisms thrive and rapidly multiply in the moist environment found in the sponge and can degrade the sponge by causing loss in sponge strength and integrity. In addition, the microorganisms can emit an odor which is unpleasant to a sponge user.

Moreover, many of these microorganisms are pathogenic thereby raising health and safety concerns. Pathogenic microorganisms such as gram negative bacteria, gram positive bacteria, yeast and fungi have all been found in sponges. Such concerns are especially relevant in the food service and medical industries where sanitization and the prevention of the spread infectious disease is of utmost importance. For example, in the food service industry, salmonella choleraesuis can be transferred to a sponge from a surface contacted by the sponge. The salmonella choleraesuis can then multiply in the sponge and be transferred to another surface thereby increasing the chance of infection.

Several attempts have been made to control or prevent the growth of these unwanted microorganisms in cellulosic sponges by treating the sponges with anti-microbial agents such as biocides. For example, U.S. Pat. No. 3,018,192 ("Hennemann et al.") discloses the use of a reaction product of a quaternary ammonium compound with either an alkali metal salt or carboxymethyl cellulose as the biocide.

U.S. Pat. No. 3,594,221 ("Baldwin") describes another process of treating fibrous materials with a germicide such as a quaternary ammonium compound. In this process, the fibrous materials are first impregnated with an acid or alkali metal montmorillonite clay. Once impregnated with the clay, the materials are infused with the germicide.

Another attempt to prevent microorganism growth in sponges and other cellulose-based products is described in EPO No. 358,572 ("Coilin"). Collin discloses a post-regenerative treatment imparting biocidal properties to porous cellulose-based products. The cellulose-based products are impregnated with a solution containing an aqueous biocide such as a quaternary ammonium compound or an oligomeric polyalkylene-2-guanide salt. The solution also contains a binder such as an acrylic latex, butadiene-styrene latex or vinylic latex. After impregnation, a second solution is contacted with the cellulose-based product. This second solution precipitates the biocidal agent onto the porous surfaces of the cellulose-based product and in addition, coagulates the binder.

A different biocidal sponge treatment described in U.S. Pat. No. 3,586,520. ("Dillon"). Dillon teaches that metal dialkyl dithiocarbamates can be utilized as biocides in pigmented sponges.

Although many cellulose sponges treated with anti-microbial agents exhibit biocidal activity, many such cellulose sponges have one or more of the following drawbacks. Some treatments impact upon the viscose xanthation, regeneration and/or subsequent rinsing processes commonly utilized in sponge manufacture. Conversely, the manufacturing process may affect the treatment rendering it ineffectual. Some anti-microbial treatments adversely affect the feel, color, flexibility, texture or water sorption properties of the sponges. In other sponges, the biocidal activity is short-lived due to numerous washings that the sponge experiences during its product life. Yet, other sponges pose a toxic threat to both the environment and to humans.

Thus, there currently exists a need for an anti-microbial agent which is capable of being dispersed or formed in a water absorbing article which can maintain long-lasting anti-microbial activity. There also exists a need for an anti-microbial agent which eliminates many adverse toxic effects to humans and the environment while maintaining long-lasting anti-microbial activity. In addition, there is a need for a anti-microbial treatment of a sponge wherein the treatment does not adversely affect the feel, color, odor, flexibility or texture of the article nor does it impact upon the xanthation, regeneration, viscose or rinsing processes commonly utilized in sponge manufacture.

SUMMARY OF THE INVENTION

The present invention comprises a metal complex which exhibits anti-microbial activity and which is capable of being dispersed or formed within a water-absorbing porous article. The metal complex comprises one or more chelating polymers, at least one transition metal ion and at least one anti-microbial potentiator.

A useful embodiment of the present invention comprises a water-absorbing porous article such as a sponge possessing durable anti-microbial activity and exhibiting minimal toxic effects to humans and the environment. The porous article of the present invention is not adversely affected by the anti-microbial complex nor does it adversely affect the anti-microbial activity of the complex.

The present invention also comprises a method of making the water-absorbing articles of the present invention.

DETAILED DESCRIPTION

The anti-microbial agent of the present invention comprises one or more chelating polymers, at least one transition metal ion and anti-microbial potentiator. This agent is capable of being dispersed or formed in a polymeric or water-absorbing article such as a sponge.

Transition metal ions are the ions of the metals classified in groups IB to VIIIB of the periodic table of elements. The metal elements are generally characterized as in having incomplete inner rings of electrons or being otherwise capable of existing in more than one valence state. The transition metals can exist in aqueous solution as cations and form ionic/covalent bonds with other species generally referred to as chelating agents or ligands. Examples of suitable metal ions are those that have coordination numbers between 2 and 8. Suitable transition metal ions include zinc, zirconium, copper and aluminum.

The transition metals of the present invention form a coordinate bond with ligands referred to as chelating polymers. It is theorized that the chelating polymers donate electrons to the ionic transition metal ion. Suitable chelating polymers include any polymer containing functional groups in close proximity capable of donating electrons. Examples of chelating polymers which can be utilized in the present invention include, but are not limited to, polyglucosamines, ethylene acrylic acid copolymers, polycarboxylic acids or polyamines. Preferred polymers include those which can have hydroxyl and/or amine groups. An especially preferred chelating polymer is the glucosamine chitosan. Chitosan is the deacetylated derivative of the polysaccharide chitin [β-(1,4)-poly-N-acetyl-D glucosamine], an abundant natural by-product of the shrimp and crab industries.

In addition to chelating with the chelating polymers, the transition metal ions are also chelated to potentiators. For the purposes of this application, a potentiator is defined as an anti-microbial agent capable of chelating to a transition metal ion. It should be noted that the selection of the potentiators is dependent upon the coordination chemistry of the metal ion. If the metal ion can be completely displaced by a potentiator, the durability of the complex within the chelating polymer can be compromised and thus, use of such potentiator is not desirable for durability purposes. Suitable potentiators include, but are not limited to, alkyl dithiocarbamates, thiazoles, imidazoles and pyrithiones.

Suitable alkyl dithiocarbamates are those wherein each alkyl group of the carbamate has up to about eight carbons. The alkyl groups can be straight or branched. Representative dithiocarbamates include dimethyl dithiocarbamate, diethyl dithiocarbamate, dipropyl dithiocarbamate, dibutyl dithiocarbamate, methyl ethyl dithiocarbamate, methyl propyl dithiocarbamate, methyl butyl dithiocarbamate, dihexyl dithiocarbamate, dioctyl dithiocarbamate and the like.

Imidazoles are a five-membered heterocylic compound which have the following structure:

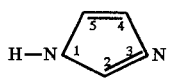

An example of a suitable imidazole is 2-(4-thiazolyl) benzimidazole.

Thiazoles are five-membered rings containing nitrogen and sulfur in the one and three positions respectively. An example of a suitable thiazole is 2-mercaptobenzothiazole.

An especially preferred potentiator is pyrithione which has the following structure:

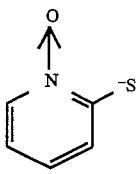

Pyrithiones are sold as zinc or sodium salts which can be obtained from the Olin Corporation under the tradename OMADINE.

If desired, natural or synthetic reinforcing fibers can be added to the article of the present invention. Suitable natural reinforcing fibers include cotton, flax, hemp, ramie, rayon, burlap, shoddy cotton, cotton linters and pulp fibers. Representative examples of synthetic fibers include polyester, nylon and acrylic fibers.

Additives can be included in the mixture to enhance specific objectives. For example, pigments, pigment fixing agents and processing aids can be added.

The sponge of the present invention can be a cellulose sponge which is prepared from viscose cellulose. The viscose cellulose can be made from any conventional viscose technique. Briefly, the viscose cellulose is commonly prepared through the mercerization and shredding of wood pulp, followed by xanthation with carbon disulfide, dilution with water and finally, mixing the mixture. After the viscose cellulose is made, crystals of sodium sulfate decahydrate, commonly referred to as Glauber's Salt, are added to the viscose cellulose. The chelating polymer and optional reinforcing fibers and/or addititives are then added. The transition metal ion, alone or in combination with the potentiator may be added to the mixture at this time although it is not necessary. After mixing the ingredients, the mixture is heated in a controlled fashion to approximately 100° C. by conductive or R.F. heating. Such heat treatment coagulates and regenerates the cellulose while melting the sodium sulfate away. The sodium sulfate is then drained and rinsed from the resultant regenerated sponge leaving a porous structure. Finally, the potentiator or transition metal ion in combination with the potentiator, if not added previously, is introduced into the article.

The sponge of the present invention can comprise from about 10 to about 90 weight percent viscose cellulose, more preferably from about 20 to 80 weight percent viscose cellulose. If added, the reinforcing fibers can comprise up to 90 weight percent of the sponge, preferably, 20 to 80 weight percent of the sponge. The amount of chelating polymer depends upon the amount of viscose cellulose added. Generally, the chelating polymer will comprise from about 0.01 to about 50 weight percent of the viscose cellulose. More preferably, the chelating polymer will comprise from about 0.1 to about 20 weight percent of the viscose cellulose. The transition metal ion may comprise from about 0.1 to about 50 weight percent of the chelating polymer and more preferably, should comprise from about 1 to about 30 weight percent of the chelating polymer. The ultimate amount of potentiator depends upon the amount of anti-microbial activity that the user wants to impart to the sponge. However, the maximum chelatable amount of the potentiator is fixed by the coordination number and/or weight percent of the transition metal ion and will therefore, preferentially lie in the range of one to four moles of potentiator per mole of transition metal ion present in the sponge.

The following examples are set forth to illustrate this invention and are not intended to limit the scope of this invention thereof.

EXAMPLES

SUBSTANTIVITY OF METAL-CHITOSAN COMPLEX THROUGHOUT THE VISCOSE SPONGE-MAKING PROCESS

PRECURSORs 1a–g

Chitosan was purchased from the Vanson Chemical Company, Redmond, Wash., in two different grades as shown in the table below:

TABLE I

| | Chitosan Grade | |
|---|---|---|
| | VNS-461 | VNS-457 |
| MW (approx) | 50,000 | 100,000 |
| Insolubles | 0.23 | 0.68 |
| Deacetylation | 92.3% | 76.4% |
| Ash | 0.12 | 0.2 |

Zinc sulfate solution was prepared by dissolving 5.5 g zinc sulfate heptahydrate in 89.5 ml deionized (DI) water. Copper sulfate solution was prepared by dissolving 4.9 g copper sulfate pentahydrate in 90.1 ml deionized water. Approximately 5 g chitosan was added to each metal salt solution, which was stirred approximately 30 minutes to disperse the chitosan, and the resulting chitosan-metal complex was filtered by suction. Each chitosan-metal filter cake was:

a) rinsed on the filter with 100 ml tap water;

b) slurried in 150 ml 1.5% NaOH, boiled 45 minutes, filtered and rinsed with 100 ml DI water; and c) rinsed on the filter with 0.3% sodium hypochlorite solution (household bleach diluted 1:15 with water) followed by a rinse with 500 ml DI water.

After each of the steps a, b, c above, samples of the filter cakes were taken for subsequent analysis. Table II below identifies each sample of chitosan-metal complex according to chitosan grade, metal ion, and process step:

TABLE II

| | Process Step | Metal/Chitosan: | | | |
|---|---|---|---|---|---|
| | | CU/461 | Cu/457 | Zn/461 | Zn/457 |
| a) | Filter cake water rinse: | 1a | 1b | 1c | — |
| b) | Filter cake boiling in NaOH + water rinse: | 1d | — | 1e | — |
| c) | Filter cake (b) bleach rinse + water rinse: | 1f | — | 1g | — |

Filter cake samples were then dried in an oven at 70°–76° C. (for 2 hours). The metal and sulfur content of the samples was determined by Inductively Coupled Plasma (ICP) analysis after digestion of the samples with acetic acid. The ICP analysis was conducted with a Model 3580 ICP Atomic Emission Spectrometer sold by Fisons Instruments of Valencia, Calif. Confirmatory analysis for metal content was performed by digestion of the samples with nitric and sulfuric acids. The metal analysis test results of the samples are reported in Table III.

TABLE III

| | Analysis | |
|---|---|---|
| Precursor # | Cu | Zn |
| 1a | 11.63% | — |
| 1b | 10.08 | — |
| 1c | — | 11% |
| 1d | 12.72 | — |
| 1e | — | 9.78 |
| 1f | 12.69 | — |

TABLE III-continued

| | Analysis | |
|---|---|---|
| Precursor # | Cu | Zn |
| 1g | — | 10.41 |
| VNS-461 (untreated) | <8 ppm | 9 ppm |

The test results indicate that the chitosan-metal complex is stable to viscose treatment. This is indicated by comparing the theoretical yield to the actual yield. Prediction of the theoretical yield is described in the following paragraph:

The chitosan glucosamine repeat unit is identical to the cellulose repeat unit except for an amine group at the C2 position. Thus, with a glucosamine repeat unit molecular weight of 157, the theoretical percent of chelated substance may be estimated depending upon the assumed mole ratio of metal ion to glucosamine unit. For example, for a mole ratio "r" of a metal M having the molecular weight "W," the theoretical percent metal in chitosan may be calculated from the equation: %=100% r.W./(157+r.W.'), assuming all repeat units are available for chelation and W is the molecular weight of the chelated compound (e.g., Zn or $ZnSO_4$). However, a characteristic typical of chitosan is its degree of deacetylation, as a result of the process from which it is made. Chitosan may have low (approximately 75%) to high (approximately 90%) degree of deacetylation. The degree of deacetylation "D" is essentially the percentage of repeat units present with —$NH_2$ functionality. Conversely, 100-D is the percentage of repeat units with —$NHCOCH_3$ functionality. If it is assumed that only repeat units with —$NH_2$ functionality may participate in chelation, then the equation predicting percent theoretical metal becomes:

$$\%=100 \cdot r \cdot D \cdot W/(D \cdot 157+(1-D)187.2+r \cdot D \cdot W')$$

Thus, for a 1:1 mole ratio of metal to glucosamine with grade VNS-462 chitosan having a D=92.3%, the theoretical percent metal for copper or zinc ranges from approximately 27%, assuming no accompanying sulfate or other ion is present, to 19%, assuming sulfate ion is present. The test results reported in Table III indicate metal contents in the 10 to 13 percent range thereby suggesting approximately a 50% efficiency relative to the maximum chelation possible.

Moreover, the metal analysis results indicate that the chitosan-metal complex is stable to the viscose sponge process insofar as both copper and zinc metal content of the samples remained relatively constant throughout the boiling caustic and bleach rinsing process.

RELATIVE DURABILITY OF CHITOSAN-PYRITHIONE AND CHITOSAN-METAL-PYRITHIONE COMPLEXES

Comparative Example 2a, Precursors 2b–c and Example 2d

Chelation of chitosan is conveniently carried out by slurrying chitosan in solutions with the desired chelation agents. The following describes the preparation of Comparative Example 2a, Precursors 2b–c and Example 2d:

a. Preparation of Comparative Example 2a (chitosan-pyrithione complex): a chitosan slurry was prepared by stirring 1 g VNS-461 into 50 g DI water. A solution of pyrithione acid (PA) was prepared in a separate flask by mixing 2.61 g 40% sodium pyrithione (NAP) solution obtained as sodium Omadine ("Omadine" is a trademark of Olin Corp, Cheshire, Conn.), with 22.4 g DI water and stirring followed by 25.28 g 1% hydrochloric acid. By this method, 99% of the NaP is acidified. The PA solution was added to the chitosan slurry, the mixture stirred 30 minutes, and the chitosan-pyrithione complex was filtered. This process was repeated four more times to yield five filter cakes of chitosan-pyrithione complex.

b. Preparation of Precursors 2b–c (metal-chitosan complex): one gram VNS-461 was stirred into a solution comprising 1.59 g $CuSO_4 \cdot 5H_2O$ dissolved in 98.4 g DI water. After stirring the slurry for 30 minutes, the chitosan-copper complex was filtered off. Similarly, a chitosan-zinc complex was prepared from 1 g VNS-461 slurried into a solution comprising 1.83 g $ZnSO_4 \cdot 7H_2O$ and 98.2 g DI water. In all, three chitosan-copper filter cakes (Precursor 2b) and six chitosan-zinc filter cakes (Precursor 2c) were prepared in this fashion.

c. Preparation of Example 2d (chitosan-zinc pyrithione complex): three of the above prepared chitosan-zinc filter cakes were, in turn, washed (on the filter) with 400 ml DI water. Each filter cake was then slurried into a solution comprising 4.75 g 40% NaP in 96.2 g DI water. This corresponds to a 2:1 mole ratio allowance of pyrithione: zinc assuming 100% coordination of the chitosan/glucosamine groups by zinc ion.

After 30 minutes stirring, the chitosan-zinc pyrithione complex was filtered.

The durability of the these chitosan complexes was determined by subjecting these complexes to typical end-use conditions such as would be expected of a sponge or wiping article in household use. Each filter cake was rinsed with water, bleach or detergent as indicated in Table IV. The cakes were thereafter tested for metal content by ICP analysis as described in Precursors 1a–g. The test results are reported in Table IV.

TABLE IV

| Filter Cake | Treatment | Metal Analysis | | |
| --- | --- | --- | --- | --- |
| | | Cu | Zn | S |
| Pyrithione acid & chitosan (Comparative Example 2a) | a | <13 ppm | <4 ppm | 2.70% |
| | b | <3 ppm | <2 ppm | 2.40% |
| | c | <9 ppm | ND | 2.10% |
| | d | <15 ppm | <34 ppm | 0.88% |
| | e | <12 ppm | <25 ppm | 0.33% |
| Copper & chitosan (Precursor 2b) | c | 13.80% | ND* | 0.52% |
| | d | 14.50% | ND | 0.74% |
| | e | 14.70% | ND | 0.48% |
| Zinc & chitosan (Precursor 2c) | c | <30 ppm | 11.04% | 0.85% |
| | d | <52 ppm | 12.08% | 0.81% |
| | e | <58 ppm | 12.01% | 0.83% |
| Zinc pyrithione & chitosan (Example 2d) | c | — | 6.46% | 6.15% |
| | d | — | 6.72% | 4.06% |
| | e | — | 6.61% | 6.34% |

*indicates below detection levels.

"Treatments" are on-the-filter rinsing as described below:
a) No rinse
b) Rinsed with 200 ml DI water
c) Rinsed with 400 ml DI water
d) Rinsed sequentially with 400 ml DI water, 200 ml 0.5% household/chlorine bleach, 200 ml DI water.
e) Rinsed sequentially with 400 ml DI water, 200 ml Spic & Span solution (3.4 g Spic & Span dissolved in 196.6 ml DI water). Spic & Span is a commercial product of Procter and Gamble Cincinnati, Ohio).

The test results revealed that the chitosan-pyrithione acid complex is minimally durable to washing with water and much less durable to bleach or detergent rinsing based on the observed decrease in sulfur content from greater than 2% to less than 1% after the latter rinsings. The copper and zinc levels remain relatively constant in the 11–15% range indicating that they are clearly durable to the rinse treatments. Due to the uptake of the pyrithione ligand, the zinc pyrithione treatment shows good durability to the rinsing, although a drop in sulfur content is noted in bleaching, possibly as a result of pyrithione displacement. The zinc level was also lowered relative to the zinc chelation cakes to 60 to 70 percent of the original level which is in agreement with theoretical predictions. For example, comparing water rinsed zinc cake to zinc-pyrithione cake, the drop from 11.5% to 6.5% zinc represents roughly a 40% reduction, in agreement with theory. This observation, taken together with the measured zinc-to-sulfur weight ratios close to unity suggests the pyrithione may be present as the doubly coordinated zinc pyrithione form. Unexpectedly, the data indicate that fully coordinated zinc pyrithione while also chelated to chitosan is stable to rinsing. For example, it is known that zinc-pyrithione occurs naturally as 2 moles of pyrithione chelated to one mole zinc. Zinc in this case has a coordination number of four and pyrithione is bidentate. These results indicate that if zinc interacts with two repeat units of chitosan, as earlier data suggest, then pyrithione is likely interacting with zinc in a monodentate fashion. The balance of zinc interaction with chitosan and pyrithione is apparently such that the entire complex exhibits stability to common rinsing. This would not be expected if either the interaction of zinc with pyrithione were weakened due to the apparent monodentate behavior, or if the interaction of zinc with pyrithione were strong enough to displace zinc from chitosan. In either case, it would be expected that either pyrithione or zinc pyrithione would have otherwise been readily rinsed out of the sponge, as observed, for example, in the case of the chitosan-pyrithione complex.

Note also, for a 1:1 mole ratio of pyrithione: glucosamine, a 0.2:1 weight ratio of sulfur: chitosan, based on one mole sulfur per mole pyrithione is expected. The results above for the chitosan-pyrithione complex indicate measured sulfur: chitosan ratios of 0.027 initially, falling an order of magnitude after detergent rinsing. Thus, for the chitosan-pyrithione case, chelation efficiency is at best approximately 14% of the maximum possible and durability is poor relative to the chitosan-metal or chitosan-zinc pyrithione cases. From the data in Table IV, it might be expected then that the use of chitosan-pyrithione complex as an antimicrobial in a sponge product is not acceptable since the active ingredient is not durable to common washing conditions.

In the following examples and precursors, cellulose sponges containing chitosan and chitosan complexes as described above were prepared and tested for durability of the complex and anti-microbial effectiveness.

Precursor 3

The cellulose sponge blocks and sample of Precursor 3 were prepared in the following manner:

Cellulose sponge was prepared by mixing together in a stainless steel kettle 14 kg viscose solution (prepared from hemlock pulp commercially available from Western Pulp Ltd., Vancouver, British Columbia) containing approximately 10% cellulose and 63.6 kg Glauber's salt with continuous stirring. Reinforcing fibers comprising 0.53 kg cellulose fiber of <12 mm staple length (Solka Floc obtained from International Filler, Tonawanda, N.Y.) and 0.3 kg rayon fiber, 12 mm staple length (obtained from Minifiber, Co., Johnson City, Tenn.) were added to the kettle (a Type 21Z universal sigma blade mixer sold by Winkworth Machinery, United Kingdom). After all ingredients had been added to the kettle, mixing was continued for an additional 30 minutes. Total volume of the mixture was approximately 76 l.

The mixture was poured into a rectangular fiberglass tank approximately 51 cm×51 cm×46 cm containing a drain spigot at the bottom and two steel electrodes, one at each opposing end of the tank. The electrodes were connected to an alternating current power source and sufficient voltage was applied to the electrodes to cause the mixture to heat to a temperature above 95° C. for of total time of 30 minutes at 105 volts AC, thus regenerating cellulose from the viscose The sponge blocks of Precursors 4 to 9 were prepared according to the method of Precursor 3 except that chitosan-metal complexes were added to the viscose mixture prior to the regeneration. The chitosan-metal complexes were prepared according to the procedure described in Precursors 1 using amounts of chitosan and metal sulfate as shown in Table V. The metal analysis results shown in Table V indicate that the amount of zinc relative to the chitosan is approximately 10% based on the weight of chitosan present, a result which is equivalent to that shown in Precursors 1 for chitosan-metal filter cake samples. This confirms that metal content survives the viscose regeneration process and subsequent water and bleach rinsing. A background level of 20–30 ppm zinc is present for all samples tested. Similar results were obtained for the sponge block containing chitosan and copper.

TABLE V

Sponge Blocks containing Chitosan complexes.

| Precursor | Chitosan (kg)(1) | Metal | $MSO_4$ (kg)(2) | % Chitosan Cellulose Cellulose (3) | % Chitosan based on final regenerated sponge solids | Metal Analysis (ppm) Zn(4) | Cu |
|---|---|---|---|---|---|---|---|
| 4 | 0.0135 | — | 0 | 1 | 0.62 | 23 | 9 |
| 5 | 0.1352 | — | 0 | 10 | 5.8 | 19 | 9 |
| 6 | 0.068 | Cu | 0.068 | 5 | 3.0 | <20 | 600 |
| 7 | 0.0135 | Zn | 0.0151 | 1 | 0.62 | 539 | <10 |
| 8 | 0.068 | Zn | 0.0755 | 5 | 3.0 | 3038 | <10 |
| 9 | 0.1352 | Zn | 0.151 | 10 | 5.8 | — | — |
| CA | 0 | — | 0 | 0 | 0 | 26 | 14 |

Notes
(1) Chitosan VNS-461 was used for all Precursors and Examples in this table except for Presursor 6 which used VNS-457.
(2) $MSO_4$ = $CuSO_4.5H_2O$ or $ZnSO_4 7H_2O$ as indicated by the metal.
(3) Calculated percent chitosan based on cellulose content of viscose solution.
(4) Metal content of sponge samples was determined by ICP analysis.

mixture. The salt solution was liberated from the mixture during the process of regeneration was drained from the bottom of the tank and the cellulose sponge block was removed from the tank and rinsed with hot tap water (approximately 55° C.) for 30 minutes. The blocks were subsequently rinsed with water, 0.3% bleach solution (sodium hypochlorite) and water again. Thereafter, after having been thoroughly squeezed between rinses to remove excess rinsate a sponge block having the dimensions of approximately 50 cm×50 cm×30 cm was obtained. The sponge block was cut into sponge samples approximately 9 cm×16 cm×3 cm.

Comparative Example A

A sponge block was prepared according to the procedure described in Precursor 3 except that after the final water rinse the block was squeezed to remove excess water and then immersed in a solution containing 0.3% alkyl benzyl dimethyl ammonium chlorides (ADBAC), a commonly used quaternary ammonium chloride disinfectant containing an alkyl group distribution of 40% $C_{12}$, 50% $C_{14}$, 10% $C_{16}$ and sold as MAQUAT MC1412 (commercially available from Mason Chemical, Arlington Hts., Ill.). The sponge block was then squeezed to remove excess rinsate, and cut into sponge samples.

Precursors 4–9

Precursors 10, 11, and 12 and Comparative Example B

Sponge samples of Precursors 10 to 12 and Comparative Example B were prepared according to methods described in Precursors 6, 7, and 8 and Control Example A respectively. The corresponding samples were dipped into running 65° C. tap water for approximately two seconds and then passed through a two-roll, zero clearance wringer having rubber rolls of 20–25 shore gauge A hardness. This process of saturating and wringing the sponge samples was repeated a total of ten times per sample. The residual zinc or copper content of each sample and obtained by ICP analysis is shown in Table VI. Comparison of metal contents in Table VI with corresponding Precursors in Table V indicate a substantial proportion of metal is bound by the chitosan even after multiple washings with water.

Comparative Example 13

Sponge samples containing 1% chitosan and no added zinc were prepared according to the procedure outlined in Precursor 4. These samples were treated with pyrithione acid (PA) as follows: 3.2 g sodium pyrithione solution (40%) were diluted with 1758 g of water. To this solution was added 42 g. of 1% sulfuric acid solution by slow addition with good stirring yielding approximately 1800 ml of dilute pyrithione acid (PA).

The sponges were then treated by a treatment hereinafter referred as the "potentiation treatment" described as follows: Sponges from prepared according to Precursor 4 were placed in a plastic bag, the PA solution was added and the bag was sealed. The sponges were squeezed several times and allowed to rest approximately five minutes. The squeeze-and-rest potentiation procedure was repeated for a total of approximately 30 minutes.

The sponge samples were then subjected to the ten rinse-and-wring cycles described in Precursors 10–12. The test results are reported in Table VI.

Example 14

Sponge samples containing 10% chitosan and no added zinc were prepared according to method described in Precursor 5. These samples were given the potentiation treatment as described in Comparative Example 13 except that the PA solution was prepared from 29.9 g 40% sodium pyrithione solution, 1385 g dilution water and 393 g. of 1% sulfuric acid. The samples were then subjected to the rinse-and-wring cycles described in Precursors 10–12. The test results are reported in Table VI.

Example 15

Sponge samples containing 1% chitosan and added zinc were prepared according to the method outlined in Precursor 7. The samples were treated with sodium pyrithione solution (NAP) as described in Comparative Example 13. The NaP solution comprised 6.3 g 40% sodium pyrithione solution diluted with 1797 g deionized water. The samples were then subjected to the ten rinse-and wring cycles described in Precursors 10–12. The test results are reported in Table VI.

Example 16

Sponge samples containing 10% chitosan and added zinc were prepared according to the method outlined in Precursor 9. These samples were treated with NaP instead of PA as described in Example 15 except that the NaP comprised 59.8 g 40% sodium pyrithione solution and 1744 g deionized water. The samples were then subjected to the ten rinse-and-wring cycles described in Precursors 10–12. The test results are reported in Table VI.

Example 17

Sponge samples prepared according to the procedure described in Precursor 4 contained 1% chitosan but with no added zinc added to the viscose mixture were treated first with zinc sulfate solution and then with NaP as follows: using the plastic bag procedure described in Comparative 13, six sponge samples from Precursor 4 were placed in a plastic bag containing approximately 1800 ml of zinc sulfate solution comprising 2.4 g $ZnSO_4 \cdot 7H_2O$ dissolved in 1800 ml DI water. After these sponge samples were squeezed and soaked for 30 minutes according to the potentiation treatment procedure, they were wrung once in the zero-clearance wringer. The sponge samples were then treated with NaP as described in Example 15 again using the potentiation treatment procedure. The samples were then subjected to the ten rinse and wring cycles described in Precursors 10 to 12.

Example 18

Sponge samples prepared according to the method of Precursor 5 contained 10% chitosan but with no added zinc were treated first with zinc sulfate solution and then with NaP as follows: using the plastic bag potentiation procedure described in Comparative Example 13, six sponge samples from Precursor 5 were placed in the plastic bag containing approximately 1800 ml of zinc sulfate solution comprising 23.1 g $ZnSO_4 \cdot 7H_2O$ dissolved in 1800 ml DI water. After these sponge samples were squeezed and soaked for approximately 30 minutes according to the potentiation procedure, they were wrung once through the zero-clearance wringer. The sponge samples were then treated with NaP as described in Example 16 again using the potentiation procedure. The samples were then subjected to the ten rinse and wring cycles described in Precursors 10–12.

Comparative Examples 19, 20

Sponge samples of Comparative Examples 19 and 20 were prepared according to the procedures described in Precursors 4 and 5 respectively. The samples were then rinsed under tap water repeatedly, sufficiently squeezed to remove excess water, and then treated with copper sulfate solution by the plastic bag potentiation technique described in Comparative Example 13.

Comparative Example 19 sponge samples were prepared by treating rinsed precursor sponge samples prepared in accordance with the procedure of Precursor 4 with copper sulfate solution which was prepared by dissolving 2.1 g $CuSO_4 \cdot 5H_2O$ in about 1800 ml DI water. These sponge samples were then subjected to ten rinse and wring cycles described in Precursors 10–12.

Similarly, Comparative Example 20 sponge samples were prepared by treating rinsed precursor sponge samples prepared in accordance with the procedure of Precursor 5 with a copper sulfate solution prepared from 20 g $CuSO_4 \cdot 5H_2O$ and 1800 ml DI. These samples also received the ten rinse-and-wring cycles.

TABLE VI

| Metal Content* of Treated Sponge Samples | | | |
|---|---|---|---|
| Example/ Precursor | Treatment | Cu(ppm) | Zn(ppm) |
| B | Water | <10 | 27 |
| 10 | Water | 622 | 8 |
| 11 | Water | <20 | 452 |
| 12 | Water | 13 | 5354 |
| 13 | PA | <4 | 4 |
| 14 | PA | 4 | 4 |
| 15 | NaP | <4 | 340 |
| 16 | NaP | 7 | 4627 |
| 17 | Zn, NaP | 1 | 300 |
| 18 | Zn, NaP | 5 | 4014 |
| 19 | Cu | 229 | 9 |
| 20 | Cu | 2530 | 9 |

*By ICP analysis

Comparison of Precursors 11 and 12 and Examples 15, 16, 17, and 18 and Comparative Examples 19 and 20 indicate that the metal content generally is near 10% of and is proportional to chitosan content which is consistent with the findings in Precursor 1. It is also interesting that the zinc content of the sponges is within 10% of the zinc content for those samples in which zinc was introduced prior to regeneration (Examples 15, 16) or after regeneration (Examples 17, 18).

Antimicrobial Activity Test Procedure

Sponge samples were tested for anti-microbial activity by measuring their "preservative effectiveness" (PE) as described below. Sponge samples were cut into strips approximately 9 cm×3 cm×1.5 cm. Each strip was inoculated with $10^6$ colony-forming units (CFU) of bacteria or $10^5$ CFU of fungi by allowing 3.0 ml inoculum to be absorbed by the sponge strip. Bacteria were chosen from the set of fourteen days storage. These results are indicated in Table VII and VIII as "Fin."

TABLE VII

Antimicrobial Activity of Sponge Samples (1)

| Example/ Comparative Examples | Metal | Treatment (2) | Ps. aeruginosa Immed | Fin | S. aureus Immed | Fin | E. coli Immed | Fin | A. niger Immed | Fin | C. albicans Immed | Fin | C. globosom Immed | Fin |
|---|---|---|---|---|---|---|---|---|---|---|---|---|---|---|
| B (3) | — | — | 0.00 | 6.62 | 0.00 | 6.82 | 3.49 | 6.98 | 2.54 | 4.93 | 5.12 | 5.12 | 3.30 | 3.48 |
| 10 | Cu | — | 0.00 | 0.00 | 0.00 | 6.82 | 0.00 | −0.06 | 2.31 | 0.00 | 0.00 | 0.89 | 2.6 | −0.03 |
| 11 | Zn | — | 0.00 | 0.00 | −0.16 | 6.82 | 0.00 | 1.22 | 2.41 | 2.42 | 0.00 | −0.89 | 2.88 | 0.53 |
| 12 | Zn | — | 0.00 | 1.12 | 0.00 | 6.52 | 1.03 | 7.07 | 2.37 | 2.52 | 0.64 | 2.10 | 2.98 | 3.35 |
| 13 | — | PA | 0.00 | 1.23 | 0.00 | 1.48 | 0.00 | 1.48 | 3.24 | 5.8 | 0.00 | 6.86 | 3.04 | 3.87 |
| 14 | — | PA | 0.00 | 2.23 | 0.00 | 3.92 | 0.00 | 3.92 | 3.33 | 5.00 | 0.00 | 4.98 | 3.38 | 4.17 |
| 15 | Zn | NaP | 0.00 | 1.82 | 0.00 | 7.08 | 0.00 | 7.08 | 3.46 | 7.41 | 0.00 | 6.86 | 2.70 | 3.23 |
| 16 | Zn | NaP | 0.00 | 2.56 | 0.00 | 6.52 | 1.03 | 7.07 | 2.42 | 6.19 | 0.65 | 6.91 | 3.56 | 4.26 |
| 17 | Zn | NaP | 0.00 | 2.44 | 0.00 | 6.52 | 1.03 | 7.07 | 2.48 | 7.41 | 0.72 | 6.91 | 3.21 | 5.94 |
| 18 | Zn | NaP | 0.00 | 1.15 | −0.17 | 6.52 | 1.03 | 7.07 | 2.45 | 2.99 | 1.01 | 5.21 | 5.95 | 5.95 |
| 19 | Cu | — | 0.00 | 0.00 | 0.00 | 6.82 | 0.00 | 0.85 | 2.34 | 2.57 | 0.00 | −0.90 | 3.00 | 3.48 |
| 20 | Cu | — | 0.00 | 5.76 | 0.00 | 5.47 | 0.00 | 5.47 | 3.27 | 4.70 | 0.00 | 6.86 | 2.65 | 3.90 |

(1) Expressed as logarithm of inoculum population reduction.
(2) Other than water rinses.
(3) Originally treated with quaternary disinfected as Control Example A.

*Pseudomonas aeruginosa* (ATCC 15442), *Staphylococcus aureus* (ATCC 6538), and *Eschericha coli* (ATCC 8739). The fungi were chosen from the set of *Aspergillus niger* (ATCC 9642), *Candida albicans* (ATTC 10231), and *Chaetomium globosum* (ATCC 6205). The inoculated strips were placed into individual, sterile, sealable plastic bags and stored at room temperature. An uninoculated sample was similarly stored as the control sample. Bacteria inoculates were stored for seven days while fungi and uninoculated samples were stored for 14 days.

Microbial growth per sponge strip was determined in the following manner. Each sponge strip was placed in a "stomacher" laboratory blender (Tekmar, Ltd, England; obtainable from Baxter Scientific Co, catalog number H3493-2), 100 ml of letheen broth was added, and the sample was processed one minute. Aliquots of the liquid were withdrawn and used to culture pour plates containing Letheen agar. The plates were incubated 48 hr at 32° C. for bacterial and 7 days at 25° C. for fungal and uninoculated samples. Using standard plate counting techniques, the number of CFU relative to the original inoculum was determined.

The difference between the inoculum count and the sample was then determined. The test results are reported as the logarithm of this difference. These treatments were then evaluated according to the standard described in U.S. Pharmacopeia, Volume XXII, 1990. A log reduction of 3.0 or greater (corresponding to reduction in microbial population of 99.9%) is considered "high" activity. A log reduction between 1.0 and 3.0 might be considered "moderate activity." Results for PE testing of sponge samples described above are shown in Table VII.

Sponge sample strips from Precursors 10–12 and Examples 13–20 were tested both for immediate activity as well as longer term antimicrobial activity. Immediate activity was determined by analyzing samples within 30 minutes of inoculation. The results are indicated in Tables VII and VIII as "Immed." For longer term activity, samples inoculated with bacteria were analyzed after seven days storage whereas samples inoculated with fungi were analyzed after

ANTIMICROBIAL ACTIVITY OF TREATED SPONGE SAMPLES AFTER LAUNDERING

Example 21

Twelve sponge samples containing chitosan and zinc were prepared according to the method described in Precursor 7. These samples were treated by the potentiation procedure as described in Comparative Example 13 with NaP solution comprising 63.1 g 40% NaP diluted with 3544 g DI water. The sponge samples were dipped into warm tap water and squeezed by hand for a total of ten repetitions. The samples were then subjected to the ten rinse and wring cycles as described in Precursors 10–12. Four of these treated sponge samples were then laundered in a household washing machine using a medium water level (approximately 15 gal), hot wash, warm rinse, and "normal" agitation speed.

Approximately 68 g of "Tide" powdered laundry detergent was added to the wash cycle. These sponges were then subjected to a final laundering cycle as just described except no detergent was added. This final cycle was intended to ensure removal of laundry detergent from the sponges. These samples are indicated as "2X" laundry cycles in Table VIII where results for PE testing are presented.

A second set of four sponge samples prepared above was laundered as described above except that four laundry cycles (including detergent) were completed followed by a fifth cycle without detergent. These samples are noted in Table VIII as "5X" laundered.

The third set of four sponges prepared above was not laundered and are designated as "OX" laundered.

Comparative Example 22

Twelve sponge samples containing chitosan and no added metal were prepared according to the procedure described in Precursor 5. These samples were treated as described in Comparative Example 13 with PA solution comprising 59.8 g 40% NaP solution diluted with 3056 g DI water to which was added with stirring a solution comprising 7.95 g 98% sulfuric acid diluted with 500 g DI water. These sponges were then rinsed and laundered as described in Example 21.

These sponge samples were then subjected to PE testing and the results were reported in Table VIII.

Comparative Example 23

Sponge samples were prepared as described in Comparative Example A. These samples were subjected to the rinse and laundering procedures of Example 21. These samples contain the quaternary disinfectant from their preparation. These samples were then subjected to PE testing and the results are shown in Table VIII.

reduction) against all tested organisms after two laundry cycles and even after five laundry cycles shows excellent activity against *C. albicans* and *C. globosum*. The latter organism has cellulolytic activity and may therefore contribute, if allowed to grow in the sponge, to the physical degradation of the sponge structure over time.

Comparative Examples 24A–D and Examples 24E–R.

The following examples and comparative examples demonstrate the durability of the chitosan-zinc-pyrithione com-

TABLE VIII

ANTIMICROBIAL ACTIVITY OF LAUNDERED SPONGES

| Ex. | Treatment | Laundered Cycles | *Ps. aeruginosa* | | *S. aureus* | | *E. coli* | | *A. niger* | | *C. albicans* | | *C. globosom* | |
|---|---|---|---|---|---|---|---|---|---|---|---|---|---|---|
| | | | Imm | Fin | Imm | Fin | Imm | Fin | Imm | Fin | Imm | Fin | Imm | Fin |
| 21 | Zn, NaP | 0X | 0.58 | 6.61 | 0.36 | 6.57 | 0.78 | 7.18 | 1.53 | 6.33 | 0.00 | 6.23 | 6.23 | 5.38 |
| | | 2X | 0.72 | 6.14 | 0.50 | 6.95 | 0.72 | 6.14 | 1.47 | 6.30 | 0.58 | 6.85 | 2.51 | 4.95 |
| | | 5X | 0.59 | −0.04 | 0.32 | −0.51 | 0.87 | 0.14 | 1.59 | 1.60 | −0.12 | 3.34 | 3.12 | 5.38 |
| 22 | PA | 0X | 0.57 | 0.59 | 0.20 | 6.57 | 0.74 | 2.07 | 1.62 | 6.33 | −0.01 | 6.23 | 2.97 | 5.38 |
| | | 2X | 0.84 | * | 0.54 | * | 0.80 | * | 1.58 | * | 0.61 | * | 4.52 | * |
| | | 5X | 0.56 | * | 0.38 | * | 0.71 | * | 1.55 | * | −0.12 | * | 3.10 | * |
| 23 | Quaternary | 0X | 0.00 | 6.62 | 6.95 | 6.95 | 6.69 | 7.41 | 1.60 | 2.95 | 1.64 | 6.85 | 3.14 | 3.57 |
| | Disinfectant | 2X | 0.00 | 0.00 | 0.39 | 0.22 | 0.81 | 0.49 | 1.44 | 2.08 | 0.51 | 6.85 | 2.45 | 3.52 |

*Sample plates not readable; contaminated by non-inoculate organisms.

The data in Table VIII indicate lack of durability towards laundering, and therefore towards normal household usage, of the quaternary disinfectant and pyrithione acid (PA) sponge treatments. Efficacy of the quaternary disinfectant against bacteria was significantly diminished by laundering. PA treatment of the sponge samples prior to laundering was highly effective against all but two bacteria. However, after laundering, the sponge samples allowed a native organism to flourish thus eliminating the possibility of reading the presence of inoculated organisms. That all sponge samples in Table VIII were rinsed and laundered similarly and separately suggest that the PA treated sponge was particularly susceptible to biological attack and perhaps more so than compared to the sponge without chitosan having been treated with water leachable quaternary ammonium disinfectant. Chitosan itself is biodegradable and, in the absence of an antimicrobial agent, either inherent or added, becomes a suitable food source for organisms.

Pyrithione acid sponge samples of Comparative Example 22 contained chitosan at 10% of the viscose cellulose whereas the zinc pyrithione sponges of Example 21 contained 1% chitosan. In many cases at 0X laundering, these were equally effective against the inoculates. However, for two important gram-negative species, *E. coli* and *Ps. aeruginosa*, the zinc pyrithione treatment was significantly superior to the PA treatment of chitosan-containing sponges. Also, at 10%, especially in dry sponges, the chitosan tends to be friable and was noticeable in the sponge as particulate matter. Aesthetically, the presence of fragmentable particulates in the sponge is unpleasant, and therefore the zinc pyrithione treatment at 1% chitosan is more to be preferred. This treatment also results in high activity (>3 log units plex in relation to viscose regeneration and more specifically in relation to the typical sponge manufacturing process. The untreated chitosan VNS-461 will be referred to as Comparative Example 24A. In a 300 cc flask, 15.6 g of $ZnSO_4 \cdot 7H_2O$ was dissolved into 162 g of DI water. After complete dissolution of the zinc salt, 8.5 g of VNS-461 grade chitosan was added and stirred 1 hr. The resulting zinc cake was filtered by vacuum and rinsed with 1000 cc DI water on the filter. One seventeenth of this cake was removed and dried at 50C for 3 hours, and will be referred to as Comparative Example 24B. The remaining zinc cake was added to a round bottom flask with 500 cc of 1.5% NaOH in DI water and boiled for 1 hr with total reflux. The cake was drained, filtered by vacuum, and rinsed with 2000 cc of DI water on the filter. One sixteenth of this cake was removed and dried at 50C for 3 hours, and will be referred to as Comparative Example 24C. The remaining cake was then added to a flask with 3000 cc of 0.3% bleach and stirred for 30 minutes. This cake was then filtered by vacuum and rinsed with 2000 cc DI water. One fifteenth of this cake was removed and dried at 50C for 3 hours, and will be referred to as sample 24D. The remaining cake was then potentiated with pyrithione by adding the cake to a flask with 33.2 g sodium pyrithione (NAP) solution (40%) and 133 g DI water. This slurry was stirred for 30 minutes, and then filtered by vacuum, and rinsed with 1000 cc DI on the filter. The cake was then split into equal 14ths, one of which was dried at 50C for 3 hours and will be referred to as sample 24E. The remaining equal 13 splits were rinsed on the vacuum filter with varying solutions and quantities as described in Table IX, and dried at 50C for 3 hours. Table IX also shows resultant Zn and S analysis which was done by ICP using nitric acid digestion of the dried samples.

TABLE IX

Example 24 sample descriptions.

| Original Cake | Treatment | Rinse | Zn | S | Example |
|---|---|---|---|---|---|
| VNS-461 | NONE | NONE | 3. ppm | ≦5. ppm | C24A |
| C24A | ZnSO$_4$ | 1000 cc DI | 9.9%** | 5.1% | C24B |
| C24B | NaOH | 2000 cc DI | 11.1% | 37. ppm | C24C |
| C24C | BLEACH | 2000 cc DI | 12.1% | ≦5. ppm | C24D |
| C24D | NaP | 1000 cc DI | 8.8% | 9.2% | 24E |
| 24E | NONE | 1000 cc DI | 9.2% | 9.6% | 24F |
| 24E | NONE | 2000 cc Di | 9.0% | 9.6% | 24G |
| 24E | NONE | 4000 cc DI | 9.5% | 10.1% | 24H |
| 24E | NONE | 1000 cc 20C tap water | 8.8% | 9.3% | 24I |
| 24E | NONE | 2000 cc 20C tap water | 9.2% | 9.6% | 24J |
| 24E | NONE | 4000 cc 20C tap water | 9.0% | 9.4% | 24K |
| 24E | NONE | 1000 cc 55C tap water | 9.7% | 10.1% | 24L |
| 24E | NONE | 2000 cc 55C tap water | 8.8% | 9.1% | 24M |
| 24E | NONE | 4000 cc 55C tap water | 9.8% | 10.3% | 24N |
| 24E | NONE | 1000 cc 1.6% Spic and Span* + 1000 cc DI | 9.7% | 10.3% | 24O |
| 24E | NONE | 1000 cc 0.5% bleach* + 1000 cc DI | 10.7% | 8.5% | 24P |
| 24E | NONE | 1000 cc 1% Comet* + 1000 cc DI | 9.8% | 10.3% | 24Q |
| 24E | NONE | 1000 cc 1% Dawn* + 1000 cc DI | 10.2% | 10.8% | 24R |

*Comet Cleanser, Dawn Dishwashing Liquid, and Spic and Span are all commercially available from Proctor and Gamble, Cincinnati OH. Clorox bleach is available from Clorox, Oakland CA.
**% = percentage by weight.

The data in Table IX indicate that zinc pyrithione is durable to these common rinses.

Comparative Examples 25 A–D and Example 25E–H

Zinc pyrithione is susceptible to discoloration due to presence of iron, as a result of chelation of free pyrithione with available iron. Out of concern that the chitosan-zinc-pyrithione complex might be susceptible to loss of pyrithione when subjected to what would be considered high iron (10 ppm) or Ca and Mg ion (300 ppm) concentrations in hard water situations, the following experiment was conducted. In a 300 cc flask, 6.4 g of ZnSO$_4$·7H$_2$O was dissolved into 67 g of DI water. After complete dissolution of the zinc salt, 3.5 g of VNS-461 grade chitosan was added and stirred 1 hr. The untreated chitosan will be referred to as Comparative Example 25A. The resulting zinc cake was filtered by vacuum and rinsed with 1000 cc DI water on the filter. One seventh of this cake was removed and dried at 50C for three hours, and will be referred to as Comparative Example 25B. The remaining zinc cake was added to a round bottom flask with 500 cc of 1.5% NaOH in DI water and boiled for 1 hr with total reflux. The cake was drained, filtered by vacuum, and rinsed with 2000 cc of DI water on the filter. One sixth of this cake was removed and dried at 50C for 3 hours, and will be referred to as Comparative Example 25C. The remaining cake was then added to a flask with 3000 cc of 0.3% bleach and stirred for 30 minutes. This cake was then filtered by vacuum and rinsed with 2000 cc DI. One fifth of this cake was removed and dried at 50C for 3 hours, and will be referred to as Comparative Example 25D. The remaining cake was then potentiated with pyrithione by adding the cake to a flask with 9.5 g sodium pyrithione (NAP) solution (40%) and 38 g DI water. This slurry was stirred for 30 minutes, and then filtered by vacuum, and rinsed with 1000 cc DI on the filter. The cake was then split into equal fourths, one of which was dried at 50C for 3 hours and will be referred to as Comparative Example 25E. The remaining equal three splits were rinsed on the vacuum filter with 4000 cc hard water solutions as described in Table X, and dried at 50C for 3 hours. Table X also shows resultant Zn and S analysis which was done by ICP using nitric acid digestion of the dried samples as described in Precursors 1a–g.

TABLE X

Comparative Examples 25A–D and Example 25E–H sample descriptions.

| Original Cake | Treatment | Rinse | Zn | S | Example |
|---|---|---|---|---|---|
| VNS-461 | NONE | NONE | 18. ppm | 26. ppm | 25A |
| C25A | ZnSO$_4$ | 1000 cc DI | 9.7%** | 5.1% | 25B |
| C25B | NaOH | 2000 cc DI | 9.6% | 39. ppm | 25C |
| C25C | BLEACH | 2000 cc DI | 10.2% | 65. ppm | 25D |
| C25D | NaP | 1000 cc DI | 7.7% | 8.1% | 25E |
| 25E | NONE | 8000 cc 20C DI | 7.1% | 7.5% | 25F |

TABLE X-continued

Comparative Examples 25A–D and Example 25E–H sample descriptions.

| Original Cake | Treatment | Rinse | Zn | S | Example |
|---|---|---|---|---|---|
| 25E | NONE | 4000 10 ppm *Fe water + 4000 cc Di | 6.5% | 7.1% | 25G |
| 25E | NONE | 4000 cc 300 ppm *Ca water + 4000 cc DI | 6.7% | 7.2% | 25H |

*10 ppm Fe water comprised of 0.2 g $FeSO_4 \cdot 7H_2O$ added to 4000 cc DI; 300 ppm Ca water comprised of 4.4 g $CaCl_2 \cdot 2\text{-}2H29$ and 4.9 9 $MgSO4O7H20$ added to 4000 cc DL
**% = percentage by weight.

The results shown in Table X indicate no significant loss of either sulfur or zinc, and thus no loss of the pyrithione moiety, for either water, iron or Ca and Mg rinses. The results further indicate the durability of the active complex.

Comparative Example 26A and Example 26B–F

In a 1000 cc flask, 33 g of $ZnSO_4 \cdot 7H_2O$ was dissolved into 342 g of DI water. After complete dissolution of the zinc salt, 18 g of VNS-461 grade chitosan was added and stirred 1 hr. The resulting zinc cake was filtered by vacuum and rinsed with 1000 cc DI water on the filter. Approximately 4 g of this damp cake was removed and dried at 50C for 3 hours, and will be referred to as Comparative Example 26A. The remaining cake was then potentiated with pyrithione by adding the cake to a flask with 76 g sodium pyrithione (NAP) solution (40%) and 304 g DI water. This slurry was stirred for 30 minutes, and then filtered by vacuum. Approximately 4 g of this damp cake was removed and dried at 50C for three hours, and will be referred to as Comparative Example 26B. The cake was then split into equal sevenths, which were washed separately on the filter with hot water and two common cleaning solutions as described in Table XI. The cakes were then dried for 3 hrs at 50C. Thereafter, the cakes were tested for metal content using the ICP analysis described in Precursors 1a–g.

These results indicate again the durability of the active chitosan-zinc-pyrithione complex.

Comparative Example 27A and Example 27B–F

Chitosan-zinc-mercaptobenzothiazole complex was prepared and rinsed with cleansing solutions in accordance with Examples 26 except instead of using sodium pyrithione for potentiation of the zinc cake, 77 g of sodium mercaptobenzothiazole (NaMBT) solution (50%) was employed with the 304 g dilution water (sodium mercaptobenzothiazole is sold commercially as NACAP from the R.T Vanderbilt Company, Norwalk Conn.). It should be noted that the resultant cake turned bright yellow upon chelation of NaMBT with the chitosan-zinc complex. Sample description and metal analysis results are presented in Table XII, and the results show the comparable durability of this active relative to the chitosan-zinc-pyrithione case.

TABLE XI

Chitosan-zinc-pyrithione sample descriptions and durability to rinsing.

| Original Cake | Treatment | Rinse | Zn | S | Example |
|---|---|---|---|---|---|
| VNS-461 | NONE | NONE | ≦25. ppm | ≦30. ppm | |
| VNS-461 | $ZnSO_4$ | 1000 cc DI | 9.8%** | 5.1% | 26A |
| 26A | NaP | NONE | 6.8% | 9.7% | 26B |
| 26B | NONE | 1000 cc 55C tap water | 8.4% | 8.6% | 26C |
| 26B | NONE | 4000 cc 55C tap water | 8.3% | 8.4% | 26D |
| 26B | NONE | 1000 cc Spic and Span + 3000 cc DI water | 7.5% | 7.5% | 26E*** |
| 26B | NONE | 1000 cc Dawn + 3000 cc DI water | 10.3% | 10.9% | 26F*** |

*Spic and Span solution comprised of 1.6 wt % Spic and Span in water; Dawn Dishwashing Liquid concentration employed was 1 wt % Dawn in water.
**% = percentage by weight.
***for samples 26E & 26F, the 3000 cc DI rinse followed the first 1000 cc rinse with cleansing solutions

TABLE XII

Chitosan-zinc-mereaptobenzothiazole sample descriptions and durability to rinsing.

| Original Cake | Treatment | Rinse | Zn | S | Example |
|---|---|---|---|---|---|
| VNS-461 | ZnSO$_4$ | 1000 cc DI | 10.3% | 5.3% | 27A |
| C27A | NaMBT | NONE | 7.6% | 13.9% | 27B |
| 27B | NONE | 1000 cc 55C tap water | 9.7% | 11.7% | 27C |
| 27B | NONE | 4000 cc 55C tap water | 10.3% | 12.2% | 27D |
| 27B | NONE | 1000 cc Spic and Span + 3000 cc DI water | 9.5% | 10.6% | 27E |
| 27B | NONE | 1000 cc Dawn + 3000 cc DI water | 10.6% | 13.0% | 27F |

Comparative Example 28A and Example 28B–F

Chitosan-zinc-dimethyldithiocarbamate complex was prepared and rinsed with cleansing solutions in accordance with Examples 26 except instead of using sodium pyrithione for potentiation of the zinc cake, 100 g of sodium dimethyldithiocarbamate (NaDMDTC) solution (30%) was employed with the 304 g dilution water (NaDMDTC is sold commercially as Vancide 51 from the R.T. Vanderbilt Company, Norwalk Conn.). It should be noted that the resultant cake became more white relative to the original light tan colored chitosan cake upon chelation of NaDMDTC with the chitosan-zinc complex. Sample description and metal analysis results are presented in Table XIII, and the results show the comparable durability of this active relative to the chitosan-zinc-pyrithione case.

TABLE XIII

Chitosan-zinc-dimethyldithiocarbamate sample descriptions and durability to rinsing.

| Original Cake | Treatment | Rinse | Zn | S | Example |
|---|---|---|---|---|---|
| VNS-461 | ZnSO$_4$ | 1000 cc DI | 10.3% | 5.2% | 28A |
| 28A | NaDMDTC | NONE | 7.3% | 21.9% | 28B |
| 28B | NONE | 1000 cc 55C tap water | 8.3% | 18.4% | 28C |
| 28B | NONE | 4000 cc 55C tap water | 8.5% | 20.2% | 28D |
| 28B | NONE | 1000 cc Spic and Span + 3000 cc DI water | 8.1% | 18.8% | 28E |
| 28B | NONE | 1000 cc Dawn + 3000 cc DI water | 8.0% | 21.0% | 28F |

Comparative Examples 29

The following example illustrates the advantage of the pre-chelation of zinc ion followed by potentiation with an antimicrobial agent in imparting durability to the active final chitosan complex. For comparison to the chitosan-zinc-potentiator complexes described in Examples 26, 27 and 28, a chitosan-pyrithione complex was prepared. A sodium pyrithione (NAP) solution was prepared by stirring 42 g of NaP solution (40%) into 1292 g DI water. To this solution was added 272 g of a 2 wt % sulfuric acid solution comprised of 5.4 g H$_2$SO$_4$ diluted in 266.6 g DI water. The acid solution was added slowly with good stirring for 30 minutes. To this resultant pyrithione acid (PA) solution was then added 16 g of VNS-461 chitosan which was allowed to stir 1 hr. This slurry was then filtered by vacuum, and 4 g of the damp cake was removed and dried at 50C for 3 hrs. This dried cake will be referred to as Comparative Example 29B.(Note: for consistency of numbering nomenclature no Comparative Example 29A has been designatied). The remaining damp cake corresponding to Comparative Example 29B was then rinsed with water and cleaning solutions by the procedure described in Example 26. Sample description and sulfur analysis results are presented in Table XIV.

TABLE XIV

Chitosan-pyrithione sample descriptions and durability to rinsing.

| Original Cake | Treatment | Rinse | Zn | S | Example |
|---|---|---|---|---|---|
| VNS-29B | PA | NONE | ≦10.ppm | 7.1% | 29B |
| 29B | NONE | 1000 cc 55C tap water | ≦10.ppm | 6.4% | 29C |
| 29B | NONE | 4000 cc 55C tap water | ≦10.ppm | 6.2% | 29D |
| 29B | NONE | 1000 cc Spic and Span + 3000 cc DI water | ≦10.ppm | 2.9% | 29B |
| 29B | NONE | 1000 cc Dawn + 3000 cc DI water | ≦10.ppm | 7.3% | 29F |

The results shown in Table XIV indicate a significant loss of sulfur and thus pyrithione when the complex was rinsed with Spic and Span cleaning solution. Thus the chitosan-pyrithione complex is seen to be considerably less durable relative to the chitosan-zinc-pyrithione complexes of Examples 26, 27 and 28.

Samples 29D, 28D, 27D, and 26D, having all received 4000 cc hot water rinsing, were then subjected to testing for antimicrobial activity using a Potato Dextrose Agar plate method as were untreated chitosan VNS-461, and samples 26A, 27A, and 28A which are the unpotentiated chitosan-zinc complexes. The procedure for this activity test is described below. Mold growth agar, sold commercially as Potato Dextrose Agar from Baltimore Biological Laboratories, was supplied as a dehydrated powder. This was rehydrated for use in cultivation of molds as per directions supplied by the manufacturer. After rehydration, the medium was sterilized by autoclaving at 121C and 15 psi for 15 minutes. To test the activity of the chitosan samples, 0.225 g of each chitosan sample was added to the bottom of sterile petri dishes, to which 22.5 cc molten Potato Dextrose Agar (PDA) was added. This resulted in approximately a 1 percent by weight amount of sample in the PDA active mixture. The chitosan and treated chitosan samples were dispersed into the agar by swirling of the solution via manual circular rotation of the plates. These suspensions were then allowed to harden in the plates by standing covered at room temperature on the benchtop. A control plate was prepared with PDA by itself. All plates were prepared in triplicates from the same sample except for the chitosan-zinc complex plates for which a single plate was prepared from samples 26A, 27A, and 28A. The plates were then inoculated with mold spores using the ASTM G21-90. The molds used included the following: *Aspergillus niger, Gliocladium virens, Aureobasidium pullulans, Chaetomium globosum,* and *Penicillium funiculosum*. The spores of these molds were dispersed into a phosphate buffer broth in equal numbers to a final mold concentration of $10^6$ spores/cc. The spores were then delivered to the prepared plates via a compressed air-driven nebulizer. The spraying continued until the plates were damp. The plates were then incubated at 28C and 95% relative humidity, and were checked daily for mold growth. Results are shown in Table XV, where the day of observed growth is recorded.

The results in Table XV show that the chitosan-zinc-potentiator complexes of either pyrithione, mercaptobenzothiazole, or dimethyldithiocarbamate resist mold growth beyond the period of the test whereas all other samples including chitosan-zinc and chitosan-pyrithione fail within this period.

TABLE XV

Potato Dextrose Agar activity test of chitosan complex actives.

| Example | Description | Days incubated until growth (failure) observed |
|---|---|---|
| PDA | control agar plate | 1 |
| VNS-461 | untreated chitosan | 1 |
| 26A, 27A, 28A | chitosan-zinc complex | 1 |
| 26D | chitosan-zinc-pyrithione | >12 |
| 27D | chitosan-zinc-mercaptobenzothiazole | >12 |
| 28D | chitosan-zinc-dimethyldithiocarbamate | >12 |
| 29D | chitosan-pyrithione | 4 |

In the next three examples and comparative examples, the utility of the chitosan-zinc-pyrithione complex in the preparation of cellulose sponge with durable antimicrobial activity is further demonstrated.

Comparative Examples 30A–D

Commercially available white (unpigmented) cellulose sponges were obtained from the O-Cel-O company, Tonawanda, N.Y. Three sponges had been rinsed with the quaternary ammonium solution as described in Comparative Example A, and had the same dimension as sponge samples described in Precursor 3. Comparative Example 30A comprised three such sponges. Three other sponges were taken and further rinsed in the following fashion. Hot 55C tap water was run over the sponges individually until the sponges were satured after which the sponges were wrung out in a zero clearance wringer having rubber rolls with 20–25 shore gage A hardness. This saturation and wringing procedure was repeated a total of 20 times. The sponge samples were then sealed in plastic bags, and will be referred to as Comparative Examples 30B. Three additional sponges were taken and given the same 20 repetition saturation and rinsing procedure as for Comparative Examples 30B, and in addition were dipped in a large beaker with 55C water flowing into it at maximum flow rate from the house supply, and wrung out in the zero clearance wringer. This procedure was repeated a total of 30 times to yield sponges which had been wrung out in the zero clearance wringer a total of 50 repetitions. These sponge samples were also sealed in bags and will be referred to as Comparative Examples 30C. Three additional sponges were selected and were rinsed in identical fashion as Comparative Examples 30C except an additional 50 repetitions of dipping in the hot water and wringing in the zero clearance wringer were made. These sponges therefore received a total of 100 repetitions of wringing in the zero clearance wringer. These sponge samples were then sealed in plastic bags and will be referred to as Comparative Examples 30D.

Examples 31A–D

A sponge block was prepared in accordance with procedures described in Precursor 7 having added zinc at 1% relative to the viscose cellulose present. Sponge samples were cut from this block as described in Precursor 3. Twelve of these sponge samples were placed in a plastic bag and were potentiated with sodium pyrithione using the potentiation treatment described in Comparative Example 13. This was accomplished by adding a dilute sodium pyrithione solution to the bag containing the sponges; the solution being comprised of 53 g of sodium pyrithione solution (40%) and 2827 g distilled water. These sponges received the 30 minute squeeze and rest procedure described in Comparative Example 13 in order to uniformly distribute the active throughout the sponge and to allow for chelation of the chitosan-zinc complex within the sponge. It was noted that immediately upon addition of the NaP solution to the bag of sponges, a purplish discoloration of the treatment solution occurred. This is believed to be due to reaction of sodium pyrithione with available iron within the sponge, which was measured to be 60 to 100 ppm in the sponge. It is well known in the art that sodium pyrithione and zinc pyrithione compounds exhibit this discoloration phenomena when contaminated with excess levels of iron, and that only a few ppm iron will show strong discoloration. This discoloration was noted to disappear after approximately ten minutes, presumably due to the preferential chelation of pyrithione with zinc in the sponge. Sponge samples were then wrung out by hand to remove excess solution. Three sponges samples were then sealed in a plastic bag and will be referred to as Example 31A. Sponge samples were rinsed in accordance with the 20, 50, and 100 repetition rinsing and wringing procedure described in Comparative Example 30, and will be referred to as Examples 31B, 31C, and 31D, respectively.

Examples 32A–D

In view of the transient discoloration observed in Example 31 due to pyrithione interaction with iron inherent in the sponge, sponge samples of Example 32 were prepared employing zinc oxide (ZnO) to prevent iron discoloration in pyrithione applications. A sponge block was prepared and subsequent cut sponge samples were treated and rinsed in accordance with the procedure described in Example 31, except that 11 g of ZnO dispersion (50%) was added to the viscose mixture prior to regeneration of the sponge block. The ZnO dispersion was obtained from the Penn Color Corporation, Doylestown Pa. When cut sponges from this block were initially wet with the sodium pyrithione solution as described in Example 31, no discoloration of the treatment solution or the sponge was observed. The sponge retained its original white appearance throughout the potentiation procedure. The treatment solution also did not become purplish throughout the treatment. The sponges were wrung out by hand and were sealed in plastic bags after receiving no rinsing, and 20, 50, and 100 rinse treatments described in Example 31. These sponge samples will be referred to as Examples 32A, and 32B, 32C, and 32D, respectively.

Sponges from this example and including samples from Comparative Example 30 and Example 31 were then subjected to the PE antimicrobial test for activity against Pseudomonas aeruginosa, as described earlier. Results for this testing are presented in Table XVI, and show the superior durability of activity for the chitosan-zinc-pyrithione sponges compared to the similarly treated commercially availables samples, Comparative Examples 30A, 30B, 30C and 30D.

In addition to the PE antimicrobial testing, sponges from this example and samples from Comparative Example 30 and Example 31 were then subjected to a test for activity against fungal growth. These sponges were tested in accordance with ASTM Method G21-90 for mold resistance. Two sets of mold were used; one set being the standard organisms designated by the ASTM method and the other set being eight molds which had been isolated from used sponges. The used sponges were collected from individuals at the O-Cel-O sponge manufacturing facility in Tonawanda, N.Y., who had acquired said sponges for use in their home. These used sponges had experienced no greater than 30 days use since their date of purchase, and had experienced a variety of uses throughout the home environment with a variety of cleaning chemicals. The fungal spores were harvested from the isolated molds which had been grown up in pure culture on PDA, and included *Aspergillus niger*, three undefined *Aspergillus species*, a *Stachybotrys species*, two undefined *Penicillium species*, and an *Alternaria species*. The ASTM designated species included *Aspergillus niger*, *Penicillium funiculosum*, *Chaetomium globosom*, *Aerobasidium pullulans*, and *Cliocladium virens*. The sponge samples were cut into 2.54 cm square pieces, and were placed in duplicate into minimal salts agar (M9) in a petri dish. The M9 agar contained essential mineral ions necessary for growth, but no carbon source. The sponges, when placed into the agar, became the sole carbon source for any mold growth seen on the plates after inoculation. The mold suspension was prepared by placing 50 μl of a $10^8$ spore/ml suspension into sterile M9 broth. For this ASTM method, equal numbers of spores were blended to yield a final total spore concentration of $5 \cdot 10^5$ spores/ml for both the ASTM designated organisms and the isolates. Spray inoculation was carried out in accordance with the procedure for the Potato Dextrose Agar activity test described in Comparative Example 29 until the surface of the sponges was damp. The plates were closed and incubated at 28C for 28 days at 95% relative humidity. The plates were checked daily for odor production and by microscopy for visual growth. Results from these tests are presented in Table XVII, where data show the days to failure after inoculation due to mold growth, days to failure after inoculation for odor production, and the final ASTM rating of the samples after the 28 day test duration. From the data it is generally observed that odor production preceded visual detection of growth (failure) by approximately one day, and thus visual detection might be considered a good measure of odor production. The rating system was as follows:

| ASTM Rating | Meaning |
|---|---|
| 0 | No growth of mold detected |
| 1 | 1–10% sample coverage by mold growth |
| 2 | 10–30% sample coverage |
| 3 | 30–60% sample coverage |
| 4 | >60% sample coverage (total sample failure) |

The data in Table XVII indicate that the ASTM and isolate molds flourished on the quaternary ammonium treated sponges, even for the cases without rinsing. The ASTM molds had only limited growth on the chitosan-zinc-pyrithione sponges, while the isolate molds showed zero growth on the same for all rinse cases. The data for the sponge containing ZnO indicates activity against molds is similar to the case without ZnO, although there appears to be some elevation in activity for the ZnO containing sponge at the intermediate 50x sponge rinsing treatment. The results confirm the superior activity and durability of the chitosan-zinc-pyrithione treatment compared to commonly employed quaternary ammonium treatment of commercially available sponge.

TABLE XVI

| Ex. | Treatment* | Water Rinses | Log Reduction Immediate | Log Reduction Final |
|---|---|---|---|---|
| 30A | Quaternary | none | −0.16 | 6.43 |
| 30B | Quaternary | 20 | −0.39 | −0.46 |
| 30c | Quaternary | 50 | −0.42 | 2.36 |
| 30D | Quaternary | 100 | −0.37 | 2.43 |
| 31A | ZP | none | 0.39 | 6.35 |
| 31B | ZP | 20 | 0.33 | 4.91 |
| 31C | ZP | 50 | 0.36 | −0.39 |
| 31D | ZP | 100 | 0.36 | −0.42 |
| 32A | ZP + ZnO | none | 0.49 | 6.35 |
| 32B | ZP + ZnO | 20 | 0.36 | 6.35 |
| 32C | ZP + ZnO | 50 | 0.49 | 6.35 |
| 32D | ZP + ZnO | 100 | 0.49 | 3.19 |

*Quaternary implies treated with quaternary ammonium solution described in Precursor 3; ZP implies containing chitosan-zinc-pyrithione complex.

TABLE XVII

RESULTS FROM MOLD RESISTANCE TESTING FOR SPONGES

| | ASTM Designated Organisms | | | Isolated Sponge Organisms | | |
|---|---|---|---|---|---|---|
| | Days to Failure | | Final ASTM | Days to Failure | | Final ASTM |
| Sample | Odor | Growth | Rating | Odor | Growth | Rating |
| 30A | 3 | 6 | 4 | 23 | 24 | 4 |
| 30B | 3 | 6 | 4 | 3 | 6 | 4 |
| 30C | 3 | 6 | 4 | 3 | 7 | 4 |
| 30D | 3 | 6 | 4 | 6 | 7 | 4 |
| 31A | >28 | >28 | 0 | >28 | >28 | 0 |
| 31B | 25 | 27 | 3 | >28 | >28 | 0 |
| 31C | 14 | 15 | 4 | >28 | >28 | 0 |
| 31D | 14 | 15 | 4 | >28 | >28 | 0 |
| 32A | >28 | >28 | 0 | >28 | >28 | 0 |
| 32B | 26 | 27 | 4 | >28 | >28 | 0 |
| 32C | 19 | 18 | 3.5 | >28 | >28 | 0 |
| 32D | 13 | 15 | 4 | >28 | >28 | 0 |

Example 33

A sponge block was prepared in accordance with the procedure described in Example 31. Sponge samples were cut and further treated as also described in Example 31 except instead of employing sodium pyrithione, potentiation of the sponge was carried out using NACAP. In this case, potentiation of four sponges in a plastic bag was carried out by addition of a solution comprised of 21.3 g of sodium mercaptobenzothiazole solution (50%) diluted with 949 g DI water. These sponges exhibited a strong yellow coloration upon contact with the NaMBT solution indicating chelation of mercaptobenzothiazole with the chitosan-zinc complex in the sponge. Sponges were then subjected to the rinsing treatments described in Comparative Example 30. The yellow coloration persisted even up to 100 rinses which indicated that the chitosan-zinc-mercaptobenzothiazole complex in the sponge was durable to such rinsing.

Example 34

Sponge samples were taken from a sponge block prepared as described in Example 31 and were further treated as also described in Example 33 except instead of employing sodium pyrithione, potentiation of the sponge was carried out using sodium dimethyldithiocarbamate (sold as Aquatreat SDM, available from the Alco Chemical Company, Chattanooga, Tenn.). In this case, potentiation of four sponges in a plastic bag was carried out by addition of a solution comprised of 20.2 g of sodium dimethyldithiocarbamate solution (40%) diluted with 948 g DI water. These sponges exhibited no discoloration of the sponge upon contact with the potentiation solution. Sponges were then subjected to the rinsing treatments described in Comparative Example 30. No change in appearance was observed even after 100 rinses.

In summary, a novel and unobvious anti-microbial composition and article incorporating the anti-microbial agent have been described. Although specific embodiments and examples have been disclosed herein, it should be borne in mind that these have been by way of explanation and illustration and the present invention is not limited thereby. Certainly modifications which are not within the ordinary skill in the art are considered to lie within the scope of this invention as defined by the following claims.

I claim:

1. A substantially water insoluble metal complex comprising:
   a. at least one chelating polymer selected from the group consisting of polyglucosamine, polycarboxylic acid, polyamine and ethylene acrylic acid copolymer;
   b. one or more metal ions chelated to said chelating polymer said metal ions selected from the group consisting of a transition metal ions, non-transition metal ions capable of existing in more than one valence state, zinc and aluminum; and
   c. at least one potentiator chelated to said transition metal ion.

2. The complex of claim 1 wherein said transition metal ion is selected from the group consisting of zinc, zirconium, copper and aluminum.

3. The complex of claim 1 wherein said chelating polymer is chitosan.

4. The complex of claim 1 wherein said potentiator is selected from the group consisting of an imidazole, a pyrithione, a thiazole and an alkyl dithiocarbamate.

5. The complex of claim 1 further including zinc oxide.

6. A substantially water insoluble metal complex comprising:
   a. at least one chelating polymer consisting of chitosan;
   b. one or more metal ions chelated to said chelating polymer said metal ions selected from the group consisting of a transition metal ions, non-transition metal ions capable of existing in more than one valence state, zinc and aluminum; and
   c. at least one potentiator chelated to said transition metal ion.

7. The complex of claim 6 wherein said potentiator is selected from the group consisting of an imidazole, a pyrithione, a thiazole and an alkyl dithiocarbamate.

8. The complex of claim 6 further including zinc oxide.

* * * * *

UNITED STATES PATENT AND TRADEMARK OFFICE
CERTIFICATE OF CORRECTION

PATENT NO.: 5,643,971

DATED: July 1, 1997

INVENTOR(S): Karl F. Roenigk

It is certified that error appears in the above-identified patent and that said Letters Patent is hereby corrected as shown below:

Column 1, line 64, "("Coilin")" should be --("Collin")--;

Column 2, line 34, "a anti-microbial" should be --an anti-microbial--;

Column 5, line 39, "b) Filter cake boiling" should be --b) Filter cake (a) + boiling--;

Column 5, line 43, "c) Filter cake (b) bleach" should be --c) Filter cake (b) + bleach--;

Column 5, line 48, "Coupled. Plasma" should be --Coupled Plasma--;

Column 6, line 36, "%=100 • r" should be --% = 100% • r--;

Column 6, line 66, "(NAP)" should be --(NaP)--;

Column 7, line 30, "of the these chitosan" should be --of these chitosan--;

Column 8, line 6, "Gamble Cincinnati" should be --Gamble, Cincinnati--;

Column 9, line 17, "for of total time" should be --for a total time--;

Column 10, Table V, fifth column heading, "% Chitosan Cellulose Cellulose" should be --% Chitosan based on Cellulose--;

Column 10, under Notes, number (2), "$ZnSO_47H_2O$" should be "$ZnSO_4 \cdot 7H_2O$";

Column 15-16, Table VIII, fourteenth column, under the title C. globosum, 1mm, "6.23" should be --2.76--;

Column 16, line 51, "(NAP)" should be --(NaP)--;

Column 18, line 42, "(NAP)" should be --(NaP)--;

UNITED STATES PATENT AND TRADEMARK OFFICE
CERTIFICATE OF CORRECTION

PATENT NO.: 5,643,971

DATED: July 1, 1997

INVENTOR(S): Karl F. Roenigk

It is certified that error appears in the above-identified patent and that said Letters Patent is hereby corrected as shown below:

Column 19, line 11, "$FeSO_4 * 7H_2O$" should be --$FeSO_4 \cdot 7H_2O$--;

Column 19, line 12, "$CaCl_2 \cdot 2H29$" should be --$CaCl_2 \cdot 2H_2O$--;

Column 19, line 12, "4.9 9 MgSO4O7H2O" should be --4.9 g $MgSO_4 \cdot 7H_2O$--;

Column 19, line 31, "(NAP)" should be --(NaP)--;

Column 21, line 63, "(NAP)" should be --(NaP)--;

Column 22, line 23, last column, "29B" should be --29E--;

Column 22, line 35, "received4000" should be --received 4000--;

Column 26, line 14, column 1, "30c" should be --30C--;

Column 26, line 45, column 2, "19" should be --18--; and

Column 26, line 45, column 3, "18" should be --19--.

Signed and Sealed this

Twenty-sixth Day of May, 1998

Attest:

BRUCE LEHMAN

Attesting Officer

Commissioner of Patents and Trademarks